United States Patent [19]

Toia

[11] 4,411,907
[45] Oct. 25, 1983

[54] ANTIINFLAMMATORY 3H-NAPHTHO(1,2-D)IMIDAZOLES

[75] Inventor: Emilio Toia, Milan, Italy

[73] Assignee: Gruppo Lepetit, S.p.A., Milan, Italy

[21] Appl. No.: 266,228

[22] Filed: May 22, 1981

[30] Foreign Application Priority Data

Jun. 6, 1980 [IT] Italy ............................... 22601 A/80

[51] Int. Cl.$^3$ .................. A61K 31/415; C07D 235/02; C07D 235/18
[52] U.S. Cl. ........................... 424/273 B; 424/248.52; 424/248.54; 424/248.56; 424/248.58; 424/250; 424/267; 424/273 R; 542/457; 542/458; 544/139; 544/370; 546/199; 548/326
[58] Field of Search ............... 548/326; 542/458, 457; 544/139, 370; 546/199; 424/273 B, 267, 250, 248.52, 248.54, 248.56, 248.58, 273 R

[56] References Cited

U.S. PATENT DOCUMENTS 4,340,607 7/1982 Toja et al. ...................... 424/273 B

FOREIGN PATENT DOCUMENTS 12866 7/1980 European Pat. Off. ............ 548/326
79-6609 12/1979 South Africa .

OTHER PUBLICATIONS

Chemical Abstracts, 68:96808x (1968) [U.S.S.R. 202,155, 9/1967, Simonov et al.].
March, J., Advanced Organic Chemistry, McGraw Hill, New York, 1968, pp. 343-344.
Houben-Weyl, Methoden der Organischen Chemie, vol. v/16, Georg Thieme, Stuttgart, 1972, p. 136.
Lown, J., et al., Can. J. Chem., 49, 1610 (1971).
Malmberg, E., et al., J. Am. Chem. Soc., 70, 2415 (1948).
Litchfield, J., et al., J. Pharm. Exp. Ther., 96, 99 (1949).
Winter, C., et al., Proc. Soc. Exptl. Biol. Med., 111, 544 (1962).
Randall, L., et al., Arch. Int. Pharmacodyn., 111, 409 (1957).
Coffey, S., (Editor), Rodd's Chemistry of Carbon Compounds, 2nd Edition, vol. I, Part B, p. 136.
Roberts, J., et al., Basic Principles of Organic Chemistry, W. A. Benjamin, New York, 1965, p. 486.

Primary Examiner—Richard A. Schwartz
Attorney, Agent, or Firm—William J. Stein; Raymond A. McDonald; Gary D. Street

[57] ABSTRACT 3H-naphth[1,2-d]imidazole derivatives of formula

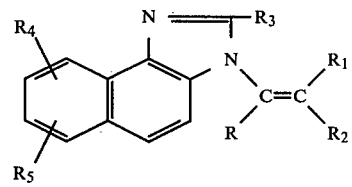

wherein R stands for hydrogen, methyl or ethyl, $R_1$ represents hydrogen, methyl or ethyl, $R_2$ represents hydrogen, methyl, ethyl, phenyl or substituted phenyl, the symbol $R_3$ stands for a phenyl radical optionally substituted and $R_4$ and $R_5$, each independently, may represent hydrogen, halogen, $(C_1-C_4)$alkyl, $(C_1-C_4)$alkylthio, $(C_1-C_4)$alkoxy or halo-$(C_1-C_4)$alkoxy, are described. Also described is the process for preparing the novel compounds, their use as antiinflammatory agents and the pharmaceutical compositions containing them.

4 Claims, No Drawings

ANTIINFLAMMATORY 3H-NAPHTHO(1,2-D)IMIDAZOLES

The present invention relates to novel 3H-naph-tho[1,2-d] imidazole derivatives of the following general formula I

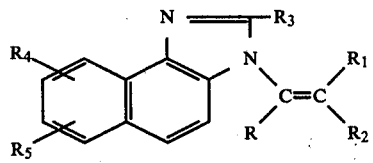

wherein R stands for hydrogen, methyl, or ethyl, $R_1$ represents hydrogen, methyl, or ethyl, $R_2$ is hydrogen, methyl, ethyl, phenyl or phenyl substituted with one to three groups independently selected from halogen, $(C_1-C_4)$alkyl, $(C_1-C_4)$alkoxy, amino, mono- and di-$(C_1-C_4)$alkylamino, $R_3$ stands for a phenyl radical optionally substituted with one to three groups independently selected from halogen, $(C_1-C_4)$alkyl, hydroxy, $(C_1-C_4)$alkoxy, $(C_3-C_4)$alkenyloxy, $(C_3-C_4)$alkynyloxy, methylenedioxy, amino, mono- and di-$(C_1-C_4)$alkylamino, $(C_2-C_4)$alkanoylamino, benzoylamino and a heterocyclic radical derived from pyrrolidine, piperidine, piperazine, $(C_1-C_4)$alkyl piperazine and morpholine; and $R_4$ and $R_5$, each independently may represent hydrogen, halogen, $(C_1-C_4)$alkyl, $(C_1-C_4)$alkylthio, $(C_1-C_4)$alkoxy, or halo-$(C_1-C_4)$alkoxy; and salts therewith of pharmaceutically acceptable acids.

The novel compounds of the present invention possess antiinflammatory, analgesic and antipyretic utility. Naphthimidazoles bearing an alkyl group at the 3-position and a substituted phenyl group at the 2-position, are known from German Pat. No. 1,137,625 which reports several thiazole, oxazole, and imidazole derivatives with photoconductive properties that can suitably be employed for electrophotographic reproduction. Moreover 3-methyl-2-(4-nitrophenyl)-3H-naphth[1,2-d]imidazole is known from the article by J. W. Lown and M. H. Akhtor published in Can. J. Chem. 49, (1971) 1610, where the authors discuss the mechanisms involved in the reaction of 1-nitroso-2-naphthylamine with 3-aroyl-aziridines. Other naphthimidazoles, substituted at the 2 and 3-positions by alkyl groups are described in U.S. Pat. No. 3,046,116 where it is said that these compounds can be conveniently used in the production of printing plates. As used herein the term "$(C_1-C_4)$alkyl" and the alkyl portion of other herein-listed radicals containing a $(C_1-C_4)$alkyl moiety identifies a straight or branched alkyl radical having from 1 to 4 carbon atoms such as methyl, ethyl, propyl, 1-methylethyl, butyl, 1-methylpropyl, 2-methylpropyl and 1,1-dimethylethyl. The expression "$(C_1-C_4)$alkoxy" identifies straight or branched alkoxy radicals having at most 4 carbon atoms which are selected from methoxy, ethoxy, propoxy, 1-methylethoxy, butoxy, 1-methylpropoxy, 2-methylpropoxy, 1,1-dimethylethoxy; and the terms "$(C_3-C_4)$alkenyloxy" and "$(C_3-C_4)$alkynyloxy" designate branched or linear 3 or 4 carbon atoms alkenyloxy and alkynyloxy groups such as 2-propenyloxy, 1-methyl-2-propenyloxy, 2-methyl-2-propenyloxy, 2-butenyloxy and 2-propynyloxy, 1-methyl-2-propynyloxy and 2-butynyloxy respectively. The term and the moiety halogen identifies chloro, bromo and fluoro.

A preferred group of compounds comprises those compounds of formula I wherein R stands for hydrogen or methyl, $R_1$ and $R_2$ are hydrogen, $R_3$ represents a phenyl radical optionally substituted with one to three groups independently selected from halogen, $(C_1-C_4)$alkyl, $(C_1-C_4)$alkoxy, amino, mono- and di-$(C_1-C_4)$alkylamino, and $R_4$ and $R_5$ are hydrogen; and salts therewith of pharmaceutically acceptable acids.

A most preferred group of compounds comprises those compounds of formula I wherein R, $R_1$ and $R_2$ are hydrogen, the symbol $R_3$ represents a phenyl ring optionally substituted with a $(C_1-C_4)$alkyl or $(C_1-C_4)$alkoxy group, and $R_4$ and $R_5$ are hydrogen; and salts therewith of pharmaceutically acceptable acids.

These acid addition salt are obtained by treating compounds of formula I above with pharmaceutically acceptable acids. As acids suitable for the formation of therapeutically acceptable salts there may be mentioned, for example, hydrohalic, sulfuric, phosphoric and nitric acids; aliphatic, alicyclic, aromatic or heterocyclic carboxylic or sulfonic acids, such as formic, acetic, propionic, succinic, glycolic, lactic, malic, tartaric, citric, ascorbic, maleic, hydroxymaleic, pyruvic acid; phenylacetic, benzoic, para-aminobenzoic, anthranilic, para-hydroxybenzoic, salicyclic, para-aminosalicylic or embonic acid, methanesulfonic, ethanesulfonic, hydroxyethanesulfonic, ethylenesulfonic acid; halobenzenesulfonic, toluenesulfonic, naphthalensulfonic acids or sulfanilic acid.

These or other salts of the new compounds may also be used for purifying the resulting compounds by converting them into salts, isolating the latter and liberating the free compounds from them. In view of the close relationship between the new compounds in the free form and in the form of their salts what has been said above and hereinafter with reference to the free compounds concerns also the corresponding salts.

The general method for preparing the novel compounds is illustrated in the following scheme.

SCHEME A

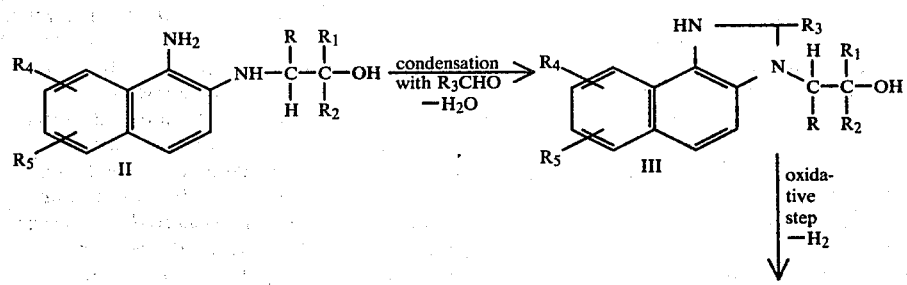

-continued
SCHEME A

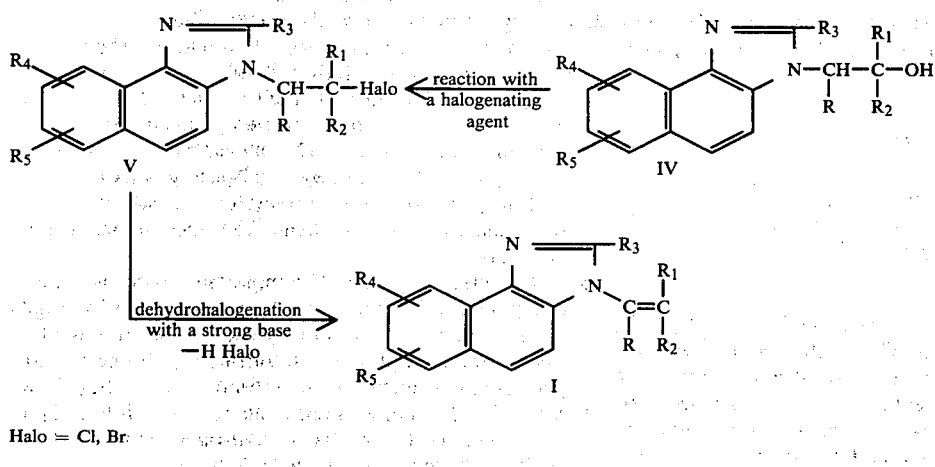

Halo = Cl, Br

This general method comprises:
(a) condensing a naphthalendiamine of formula II with a suitably selected aldehyde of formula R₃CHO, (b) oxidizing the intermediate imidazoline II to the corresponding naphthimidazole derivative IV,
(c) reacting the intermediate IV with a halogenating agent to give the corresponding halo derivative of formula V, and finally,
(d) dehydrohalogenating the intermediate of formula V with a strong base to give the final compound of formula I.

Widely varying conditions can be used to bring about the condensation between the naphthalendiamine II and the aldehyde R₃CHO; however rather good results have been obtained adding an equimolecular proportion or a slight excess of the aldehyde to a solution of the compound of formula II in an inert high boiling organic solvent such as for instance xylene, toluene, or cymene and then refluxing the obtained reaction mixture in a Dean-Stark apparatus under inert atmosphere.

As for the oxidative step which in the above scheme is visualized as a simple dehydrogenation, it can be performed in the presence of a mild oxidizing agent, such as for instance manganese dioxide or cupric acetate, or better with a dehydrogenating agent suitably selected from the group of metals or metal oxides generally employed and named as "hydrognenating catalysts" such as for instance Palladium, Platinum, Ruthenium, Rhodium, Platinum dioxide, either in powder form or adsorbed on a charcoal or asbestos carrier, and Raney-Nickel. The obtained reaction products are recovered by conventional procedures which involve filtration of the hot solution and evaporation of the solvent under reduced pressure. Purification of the raw material thus obtained is achieved simply by crystallization or by means of chromatographic techniques.

The transformation of the 3-(2-hydroxyethyl)naphthimidazole derivative IV into the corresponding 3-(2-haloethyl)naphthimidazole of formula V is carried out using an inorganic acid halide such as for instance, SOCl₂, PCl₅, PBr₅, PCl₃, PBr₃, and POCl₃, and preferably SOCl₂.

More particularly this reaction smoothly proceeds by dripping a slight excess of the halogenating agent into a solution of the intermediate IV in an inert organic solvent and then refluxing the reaction mixture for a short time.

Finally dehydrohalogenation of the intermediate V to give the end compound of formula I is achieved by means of a strong base such as for instance an alkali metal hydride, in the presence of an inert organic solvent such as for instance tetrahydrofuran, dioxane, and the like.

The end compound I is recovered by pouring the reaction mixture in ice/water, making the aqueous solution slightly acidic, and separating the precipitate which forms, that is then purified according to conventional procedures.

The starting naphthalendiamine derivatives of formula II are generally novel and may be prepared through different routes.

The process we have generally employed for preparing the starting naphthalendiamine derivatives involves the reduction of a N-substituted-1-nitroso-2-naphthaleneamine of formula

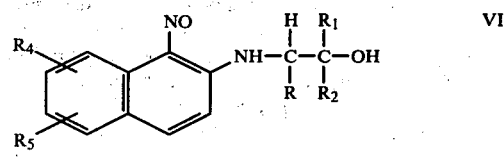

wherein R, R₁, R₂, R₄ and R₅ are as defined before, by means of hydrogen gas in the presence of a hydrogenating catalyst.

Various hydrogenation catalysts may be employed to bring out the conversion to diamines and generally the same metals and metal oxides employed in the oxidative step of scheme A are preferably used, i.e. Palladium, Platinum, Ruthenium, Rhodium, Platinum dioxide, either in powder form or adsorbed on a carrier, and Raney-nickel. Also the reaction conditions may vary widely since all the catalysts listed above are active, and are preferably used, at room temperature and atmospheric pressure but can suitably be employed also up to 4 atmospheres. Solvents which can conveniently be employed in this reaction are selected from lower aliphatic alcohols such as methanol and ethanol and aromatic hydrocarbons such as for instance benzene, toluene, xylene and cymene.

The starting nitroso compounds have been synthetized through reaction of primary amines of formula $H_2N$-CHR-$CR_1R_2OH$ with 1-nitroso-2-naphthol according to the method described by E. W. Malmberg and C. S. Hamilton in J. Am. Chem. Soc. 70, 2415 (1948). The starting amines are either commercially available products or can be prepared according to the conventional methods known in chemistry.

The above reported method for preparing the starting naphthalenediamines II from the corresponding N-substituted-1-nitroso-2-naphthaleneamines is of particular value for many reasons. First of all infact the reduction reaction does not require drastic conditions but on the contrary it proceeds rapidly at room temperature and atmospheric pressure, secondly the reaction conditions themselves, the solvents and the starting nitroso-compounds employed are particularly safe from the industrial point of view; thirdly the naphthalenediamines thus obtained are not necessarily separated from the reaction mixture and the condensation with the suitably selected aldehyde $R_3CHO$ can be carried out without any working up of the reaction mixture containing the hydrogenated compound of formula II before adding the aldehyde $R_3CHO$. In this case, if separation of the naphthalenediamines is not required, also the reduction of the N-substituted-1-nitroso-2-naphthaleneamines will be carried out in an inert high boiling organic solvent. Moreover, since catalyzed reduction, which takes place on the catalyst's surface, is a reversible process, the same catalysts employed for reducing the nitrosonaphthaleneamines can be conveniently employed in the absence of hydrogen, in the dehydrogenation procedure. Furthermore, some compounds of formula I may be obtained also through chemical modifications of other compounds, falling within the same formula I, prepared according to the reaction scheme outlined before. Thus for instance compounds of formula I wherein $R_3$ stands for a phenyl group bearing a ($C_1$-$C_4$)alkoxy, ($C_3$-$C_4$)alkenyloxy or ($C_3$-$C_4$)alkynyloxy substituent can be prepared by reacting the corresponding compounds of formula I wherein $R_3$ stands for phenyl substituted with hydroxy with ($C_1$-$C_4$)alkyl, ($C_3$-$C_4$)alkenyl or ($C_3$-$C_4$)alkynyl halogenides or sulfates. Moreover, compounds wherein $R_3$ is an aminophenyl group may be easily prepared from the corresponding alkanoylamino- and benzoylamino-phenyl derivatives by acid hydrolysis. A convenient route leading to monoalkylaminophenyl compounds in high yields, consists in preparing the sodium derivative of the amidic nitrogen atom of a corresponding acylamino derivative, then substituting it by means of an alkylating agent and finally splitting off the protecting acyl group by alkaline hydrolysis. It is intended that alternative methods which can suitably be employed for transforming a pre-existing radical into another falling within the given meanings, although not specifically disclosed, are to be considered within the scope of the present invention.

As stated before, the novel compounds of the present invention are active as antiinflammatories and analgesics. These biological activities are coupled with a low toxicity since the approximate $LD_{50}$ per os in mice are generally higher than 1000 mg/kg. The toxicities were determined according to Lichtfield and Wilcoxon, Journ. Pharm. Expt. Ther., 96, 99, (1949).

The antiinflammatory activity was ascertained by means of the carrageenin-induced oedema test in rats; according to this test, which was carried out by following the methology described by C. A. Winter et al., in Proc. Soc. Exptl. Biol. Med. 111, 544, (1962), the ability of the compounds of the invention to reduce the oedema induced in the rat paw by injection of carrageenin was evaluated. The compound of example 1, when tested at the oral dose of 200 mg/kg which corresponds to less than 1/5 of the corresponding $LD_{50}$, caused a percent decrease of the induced oedema of 58.

The antiinflammatory activity is coupled also with interesting analgesic properties.

Analogesia was investigated according to the method described by Randell et al. in Arch. Int. Pharmacodyn. 111, 409, (1957). It is finally to be noted that the new naphthimidazoles which are the object of the present invention display a very low ulcerogenic activity which is several times lesser than the one observed with other known and therapeutically used antiinflammatory substances. The ulcerogenic action was determined according to Thuillier et al. Chim. Ther. 3, 51, (1968). The use of the novel compounds as antiinflammatory agents is therefore a further specific object of the present invention. The term "use" is intended to refer to all industrially applicable aspects and acts of said use including the embodying of the novel compounds or their salts into pharmaceutical compositions.

For antiinflammatory use the compounds of the invention may be administered by different routes. While the preferred routes of administration are oral and rectal, parenteral administration can also be employed. For oral administration the compounds of the present invention are compounded into pharmaceutical dosage forms such as for instance tablets, capsules, elixirs, solutions and the like. Tablets may containg in addition to the therapeutic ingredient the usual additives such inert diluents, for example starch, lactose, kaolin, calcium phosphate, mannitol and the like; binders, for example gelatin, starch, sugars, gums, carboxymethylcellulose, polyvinylpyrrolidone, and the like; lubricants, for example talc, magnesium stearate, stearic acid and the like; and the commonly employed disintegrant, coloring, sweetening and flavoring agents. Coated or hard-shell capsules may also be prepared which may contain the same additives indicated above for tablets. Liquid preparations such as elixirs and solutions are prepared by dissolving the active ingredient in an aqueous or non-aqueous pharmaceutically acceptable solvent and may contain also suspending, sweetening, flavoring, and preservative agents as known in the art.

For rectal administration the compounds are formulated as suppositories wherein the active ingredient is admixed with conventional vehicles such as for example cocoa butter, wax, spermaceti or polyoxyethylenglycols and their derivatives.

The dosage range is from about 0.05 to about 10.0 g per day, preferably administered in divided doses. Accordingly, the present invention provides a pharmaceutical composition for antiinflammatory use comprising from about 50 to about 1000 mg of a compound of the invention as the active ingredient together with a pharmaceutically acceptable carrier.

The following example is given to illustrate the process for preparing the compounds of the invention but it should not be considered as a limitation to the scope of the invention.

EXAMPLE 1

3-Ethenyl-2-(4-methoxyphenyl)-3H-naphth[1,2-d]imidazole.

N-(2-hydroxyethyl)-1-nitroso-2-naphthalenamine (12.97 g, 0.06 mole) in toluene (1300 ml) is hydrogenated at room temperature and atmospheric pressure in the pressence of 5% Palladium-on-carbon (2.6 g).

After 75 minutes, when the theoretical amount of hydrogen has been consumed, 4-methoxybenzaldehyde (8.16 g, 0.06 mole) is added and the obtained reaction mixture is refluxed in a Dean-Stark apparatus under nitrogen stream for 3 hours. 400 ml of binary azeotrope water/toluene are discarded and replaced by 400 ml of fresh toluene. Then further 4.1 g of 5% Palladium-on-carbon are added and reflux is prolonged for additional 6 hours. The hot solution is filtered in order to remove the catalyst, the filtrate is concentrated to dryness and the thus obtained residue is crystallized from methanol yielding 14.3 g (75%) of 3-(2-hydroxyethyl)-2-(4-methoxyphenyl)-3H-naphth[1,2-d]imidazole.

3-(2-Hydroxyethyl)-2-(4-methoxyphenyl)-3H-naphth[1,2-d]imidazole (9.14 g, 0.028 mole) in anhydrous chloroform (600 ml) is heated to the reflux temperature with stirring and a solution of $SOCl_2$ (2.3 ml, 0.031 mole) in chloroform (20 ml) is added thereto. When the addition is terminated, the reaction mixture is refluxed for further 20 minutes. The solvent is then removed and the residue is taken up with water and made basic by the addition of a $NaHCO_3$ solution. The solid is recovered by filtration, dried under vacuum and crystallized from ethanol. Yield 98% (9.3 g).

5.3 g (0.016 mole) of the obtained product in anhydrous tetrahydrofuran (250 ml) are heated to 60° C. until a solution is obtained; then the temperature is lowered to room temperature and sodium hydride (2.1 g, 0.064 mole) is gradually added with stirring. The reaction mixture is refluxed for 3 hours, then dimethylformamide (100 ml) is added thereto and heating is prolonged for further 3 hours. Tetrahydrofuran is boiled off, and the reaction mixture is poured into ice/water (1500 ml), the solution is brought to pH 4 by the addition of acetic acid (20 ml) and the precipitate formed is recovered by filtration. This solid is dissolved in methylene chloride, dried over $MgSO_4$, filtered and evaporated to dryness giving a residue which is crystallized from cyclohexane. Yield 87% (4.2 g). Two different crystalline forms were evidentiated by Thermal Analysis melting at 85° C. and 96° C.

| Elemental analysis | C | H | N |
|---|---|---|---|
| Calculated for $C_{20}H_{16}N_2O$ | 79.98 | 5.37 | 9.33 |
| Found | 79.64 | 5.34 | 9.26 |

Essentially the same procedure described in the foregoing example may satisfactorily be used to prepare the following compounds:

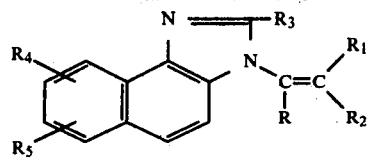

| Ex. | R | $R_1$ | $R_2$ | $R_3$ | $R_4$ | $R_5$ |
|---|---|---|---|---|---|---|
| 2 | H | H | H | phenyl | H | H |
| 3 | —CH₃ | H | H | 4-OCH₃-phenyl | H | H |
| 4 | —CH₃ | H | H | phenyl | H | H |
| 5 | —CH₃ | —CH₃ | H | 4-OCH₃-phenyl | H | H |
| 6 | —CH₃ | —CH₃ | —CH₃ | 4-OCH₃-phenyl | H | H |
| 7 | H | —CH₃ | —CH₃ | 4-OCH₃-phenyl | H | H |

-continued
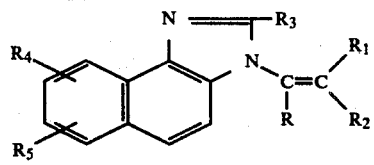
| Ex. | R | R₁ | R₂ | R₃ | R₄ | R₅ |
|---|---|---|---|---|---|---|
| 8 | H | H | –C₆H₅ | –C₆H₄–OCH₃ | H | H |
| 9 | H | H | –C₆H₄–CH₃ | –C₆H₄–OCH₃ | H | H |
| 10 | H | H | –C₆H₄(OCH₃) | –C₆H₄–OCH₃ | H | H |
| 11 | H | H | –C₆H₅ | –C₆H₅ | 7-OCH₃ | 8-OCH₃ |
| 12 | H | H | H | –C₆H₃(OCH₃)₂ | H | H |
| 13 | H | H | H | –C₆H₃(CH₃)₂ | H | H |
| 14 | H | H | H | –C₆H₄–Cl | H | H |
| 15 | H | H | H | –C₆H₄–NMe₂ | H | H |
| 16 | H | H | H | –C₆H₄–NHCOCH₃ | H | H |
| 17 | H | H | H | –C₆H₂(OCH₃)₂(NMe₂) | H | H |
| 18 | H | H | H | –C₆H₄–OCH₃ | 7-OCH₃ | H |

-continued

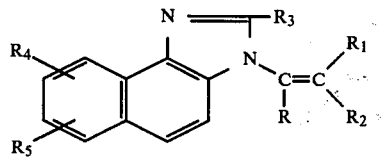

| Ex. | R | R₁ | R₂ | R₃ | R₄ | R₅ |
|---|---|---|---|---|---|---|
| 19 | H | H | H | —⌬—OCH₃ | 7-SCH₃ | H |
| 20 | H | H | H | —⌬—N(piperazine)N—CH₃ | H | H |
| 21 | H | H | H | —⌬—OCOCH₃ | H | H |
| 22 | H | H | H | —⌬(CH₃)—NMe₂ | H | H |
| 23 | H | H | H | —⌬—O—CH₂CH₃ | H | H |
| 24 | H | H | H | —⌬—OCO—⌬ | H | H |
| 25 | CH₃ | H | H | —⌬(CH₃)(CH₃)—NMe₂ | H | H |
| 26 | CH₃ | CH₃ | H | —⌬—OCH₃ | 7-OCH₃ | 8-OCH₃ |
| 27 | CH₃ | H | —⌬—Cl | —⌬—OCH₃ | H | H |

EXAMPLE 28

A tablet is prepared from 3-ethenyl-2-(4-methoxyphenyl)-3H-naphth[1,2-d]imidazole: 500 mg starch: 40 mg talc: 10 mg magnesium stearate: 10 mg

EXAMPLE 29

A tablet is prepared from 3-ethenyl-2-(4-methoxyphenyl)-3H-naphth[1,2-d]imidazole: 300 mg lactose: 50 mg microcrystalline cellulose: 50 mg stearic acid: 10 mg colloidal silica: 5 mg

EXAMPLE 30

3-ethenyl-2-(4-methoxyphenyl)-3H-naphth[1,2-d]imidazole: 400 mg talc: 40 mg sodium carboxymethylcellulose: 40 mg starch: 120 mg

I claim:

1. A 3H-naphtho[1,2-]imidazole derivative having the formula

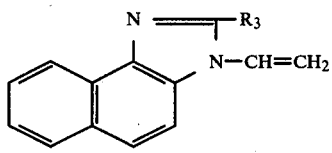

wherein $R_3$ represents a phenyl radical optionally substituted with 1 to 3 groups independently selected from $(C_1-C_4)$ alkyl and $(C_1-C_4)$ alkoxy; or a salt thereof with a pharmaceutically acceptable acid.

2. A compound according to claim 1 which is 3-ethenyl-2-(4-methoxyphenyl)-3H-naphth-[1,2-d]imidazole.

3. An antiinflammatory or analgesic composition in dosage unit form which comprises from about 50 to about 1000 mg of a compound of claim 1, or an acid addition salt thereof, in admixture with a pharmaceutical carrier.

4. An antiinflammatory or analgesic composition according to claim 3 wherein the compound of claim 1 is 3-ethenyl-2-(4-methoxyphenyl)-3H-naphth[1,2-d]imidazole.

* * * * *